United States Patent
Raes et al.

(10) Patent No.: US 11,406,678 B2
(45) Date of Patent: Aug. 9, 2022

(54) SIMMONDSIN FORMULATION

(71) Applicants: Stefaan Raes, Merelbeke (BE);
Herman Van Den Driessche, Oudenaarde (BE)

(72) Inventors: Stefaan Raes, Merelbeke (BE); André D'Oosterlynck, Oudenaarde (BE)

(73) Assignees: Stefaan Raes, Merelbeke (BE); Herman Van Den Driessche, Oudenaarde (BE)

(*) Notice: Subject to any disclaimer, the term of this patent is extended or adjusted under 35 U.S.C. 154(b) by 397 days.

(21) Appl. No.: 16/178,850

(22) Filed: Nov. 2, 2018

(65) Prior Publication Data
US 2019/0070238 A1   Mar. 7, 2019

Related U.S. Application Data

(63) Continuation-in-part of application No. PCT/IB2017/000485, filed on Apr. 27, 2017, which is a continuation of application No. PCT/IB2016/000580, filed on May 4, 2016.

(51) Int. Cl.
| | |
|---|---|
| *A61K 36/00* | (2006.01) |
| *A61K 36/185* | (2006.01) |
| *A61K 31/7034* | (2006.01) |
| *A23L 33/105* | (2016.01) |
| *A61K 31/277* | (2006.01) |
| *A61K 9/48* | (2006.01) |
| *A61K 9/107* | (2006.01) |
| *A23L 33/135* | (2016.01) |
| *A61P 27/02* | (2006.01) |
| *A61P 25/28* | (2006.01) |
| *A61P 17/00* | (2006.01) |
| *A61P 19/02* | (2006.01) |
| *A61P 25/16* | (2006.01) |
| *A61P 35/00* | (2006.01) |
| *A61K 31/192* | (2006.01) |

(52) U.S. Cl.
CPC .......... *A61K 36/185* (2013.01); *A23L 33/105* (2016.08); *A23L 33/135* (2016.08); *A61K 9/1075* (2013.01); *A61K 9/4808* (2013.01); *A61K 9/4858* (2013.01); *A61K 9/4875* (2013.01); *A61K 9/4891* (2013.01); *A61K 31/192* (2013.01); *A61K 31/277* (2013.01); *A61K 31/7034* (2013.01); *A61P 17/00* (2018.01); *A61P 19/02* (2018.01); *A61P 25/16* (2018.01); *A61P 25/28* (2018.01); *A61P 27/02* (2018.01); *A61P 35/00* (2018.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 4,855,139 | A * | 8/1989 | Srinivasan | A61L 15/46 424/404 |
| 7,387,999 | B2 | 6/2008 | D'Oosterlynck et al. | |
| 8,034,589 | B2 * | 10/2011 | Kosai | C12N 7/00 435/91.4 |
| 2004/0253647 | A1 * | 12/2004 | Mathews | A61P 25/16 435/7.2 |
| 2015/0216203 | A1 | 8/2015 | Isaksen et al. | |
| 2015/0238589 | A1 * | 8/2015 | Gunn | A61K 39/05 424/257.1 |

FOREIGN PATENT DOCUMENTS

| | | |
|---|---|---|
| EP | 0046723 | 3/1982 |
| WO | 2004004746 | 1/2004 |

OTHER PUBLICATIONS

Cokelaere et al. ("Influence of Pure Simmondsin on the Food Intake in Rats", J. Aric. Food Chem. 1992, 40, pp. 1839-1842). (Year: 1992).*
International Search Report in corresponding PCT/IB2017/000485, dated Dec. 12, 2017.
Al-Qizwini, et al., "Cytotoxic Effects of Jordanian Simmondsia Chinensis (Link) C.K. Schneid on Different Cancer Cell Lines", European Scientific Journal, Aug. 2014, edition vol. 10, No. 24.
Cole, et al., "Enteric coated HPMC capsules designed to achieve intestinal targeting", Inter. J of Pharmaceutics, vol. 231, 2002, pp. 83-95.
Sobby, et al., "Some Biological and Pharmacological Studies on Jojoba Oil" Bulletin of the Faculty of Pharmacy (Cairo University), vol. 34, No. 3, 1996, pp. 239-243, XP002929497.
Cokelaere, et al., "Influence of Pure Simmondsin on the Food Intake in Rats", J. Agric. Food Chem., 1992, vol. 40, pp. 1839-1842.

* cited by examiner

*Primary Examiner* — Michael Barker
*Assistant Examiner* — Randall O Winston
(74) *Attorney, Agent, or Firm* — Hovey Williams LLP

(57) ABSTRACT

A human oral at least partly enteric formulation comprising one or more jojoba components, for controlling, stimulating or modulating functions for patients suffering from a degenerative disease, or for patients at risk from suffering from a degenerative disease, or for patients under therapeutic treatment of a degenerative disease.

15 Claims, No Drawings

SIMMONDSIN FORMULATION

CROSS-REFERENCE TO RELATED APPLICATIONS

The present application is a continuation-in-part of PCT/IB2017/000485, filed on Apr. 27, 2017, and published under number WO2017/191501, which claims the priority benefit of PCT/IB2016/000580, filed on May 4, 2016, each of which is incorporated by reference in its entirety herein.

BACKGROUND OF THE INVENTION

Field of the Invention

The present invention relates to an oral formulation comprising one or more jojoba components, as well as at least one enzyme suitable to splice off the glucose moiety of one or more Jojoba components.

Description of Related Art

The use of simmondsin molecules for use as angiogenesis inhibitor is disclosed in U.S. Pat. No. 7,387,999 (assignee: D'OOSTERLYNCK André). The content of said patent is incorporated in the present specification by reference. Said US patent corresponds to PCT application WO2004/004746 and EP1526862.

"Influence of Pure Simmondsin on the food Intake in rats", Cokelaere et al, J. Agric. Food Chem 1992, 40, 1839-1842 discloses a study on rats fed with acetate buffer, simmondsin and simmondsin derivative. The dose administered in said study was very high, as being 25 mg or 50 mg simmondsin per kg body weight. In a first test, it was shown that weight loss was only due to the lower food intake, simmondsin as such having no effect on the weight loss. In another test using simmondsin preincubated with Beta-glucosidase for 45 minutes, it appears that for a group of two rats, the feeding of pre-incubated simmondsin with Beta-glucosidase generates a higher reduction of weight loss. Said study has also shown that when stopping the feeding with simmondsin, the food intake was increased for rats previously fed with food containing simmondsin. It has turned out that the weight loss was correlated to the feeding of an exorbitant high dose of simmondsins, and that the weight loss observed on rats was considered as a side effect only observed in abnormal high doses. Said article does not teach, nor suggest any curing properties against cancer, arthritis, etc.

Indeed, no reference at all is made in said study for treating or preventing troubles due to degenerative diseases, such as cancer, sarcoidosis, Kahler's disease, arthritis, skin disease, Alzheimer, Parkinson, amyotrophic lateral sclerosis (ALS), AIDS, Huntington's disease, eye disease.

EP 0046723 discloses to a method for preparing isomerates of jojoba oil, by submitting jojoba oil to a heat treatment at a temperature of 150 to 350° C. in presence of an acidic bentonite clay. The so prepared isomerates are used in homogeneous composition, which can be used in various fields, such as cosmetics, polishing waxes, non stick spray for baking pans. No reference is made to the use of said isomerates for treating patient suffering from troubles, such as cancer and skin diseases.

"Cytoxic Effects of Jordanian *Simmondsia Chinensis* (Link) C. K. Schneider on Different Cancer Cell Lines", Al-Qizwini H. et al, European Scientific Journal, August 2014, vol 10, No. 24, pages 182 to 195 discloses a study relating to the effect of total extracts of Jojoba leaves, seeds and oil on the growth of various cancer cell lines.

"Some Biological And Pharmacological Studies on Jojoba Oil" Sobhy H. et al, Bull Fac Pharma Cairo Univ., Vol 34 No. 3, 1996 discloses that crude Jojoba oil has no effects on yeast and fungi, but had an antimicrobial effect on *Bacillus Subtilis, Staphylococcus aureus, Proteus vulgaris* and *Proteus mirabilis*, but no antimicrobial activity on *Pseudomonas aeruginosa*, nor on *Escherichia coli*.

It has been observed that many human diseases are linked with over stimulation of the basic Fibroblast Growth Factor, such diseases being for example cancers and rheumatism or arthritis. It seems that patients suffering of one of such diseases connected to an over stimulation of Fibroblast Growth Factor are also at high risk to suffer from other of such diseases. (see Hellgren et al, "Do Rheumatoid Arthritis and lymphoma share risk factors? A comparison of lymphoma and cancer risks before and after diagnosis of Rheumatoid Arthritis.—Arthritis and Rhumatism 62 (5), 1252-1258).

The said later prior art discloses a pharmaceutical composition formulated for oral administration.

It has been shown now that when administering composition releasing the active agent already in the stomach, higher doses were required for achieving some benefits in treating patients, while some patients developed some side effects, like higher blood pressure, higher heartbeat, etc.

The invention relates to a composition for ensuring an angiogenesis modulation, so as to maintain a good balance between stimulating and suppressing new blood vessel formation. If for some diseases or lesions, like atherosclerosis and ischemic lesions, stimulation of angiogenesis is beneficial, too high uncontrolled blood vessel development is detrimental for pathologies like tumor progression and metastasis.

According to McMahon G (2000), VEGF Receptor Signaling in Tumor Angiogenesis, The Oncologist 5 (Suppl. 1): 3-10, Vascular Endothelial Growth factor (VEGF) plays a key role in the control of the angiogenesis phenomenon, VEGF and its receptor being first targets in the development of anti-angiogenetic drugs for cancer treatment. Tyrokinase inhibitors (Bevacizumab, Sunitinib, etc) blocking the VEGF receptor have already been proposed in combination with other chemotherapeutics. Clinical tests result give quite moderate success in progression free survival, and low success in overall survival. It is expected that tumours actually slow down upon cutting of their blood supply due to angiogenesis inhibition, but that said angiogenesis inhibition creates a state of local hypoxia. Due to an expected symbiosis existing between oxygenated cancer cells and hypoxygenated cancer cells, the lactate produced by the anaerobic glucose combustion by the hypoxygenated cancer cells is suitable as energy source for oxygenated cancer cells, via an oxidative pathway. Due to said energy source, the tumor recovers mostly through a pathway re-establishing angiogenesis, expected through activation of the Fibroblast Growth Factor (FGF) receptors.

Said tyrokinase inhibitors have also some toxic effects and detrimental side effects, on top of the chemotherapeutics alone.

Since FGF can be considered by cancer cells as a rescue option for their development when the VEGF-pathway is no longer profitable, FGF could be a good potential target candidate for angiogenesis control.

It has now been observed that by controlling the release of some jojoba components (especially of Formula I and/or II) within and/or after the small intestine tract (and not in the stomach), it was possible to stimulate the p53 gene function and/or to modulate the Fibroblast Growth Factor and/or to modulate the angiogenesis phenomenon and/or control mammal (especially human, dog and cat) intestinal in a mammal (human or dog or cat) suffering from degenerative disease, with less side effects or with side effects with lower intensity, with respect to the administration of known drugs for treating the same degenerative disease with same efficiency.

The invention enables thus a safer use, with better treatment and less side effects, with low daily active agent doses, the delivery of the active agent(s) being better targeted in the intestine tract.

DESCRIPTION OF THE INVENTION

The invention relates to mammal (especially human, dog and cat, more specifically human) oral at least partly enteric formulation comprising one or more jojoba components comprising a glucose moiety, said formulation being adapted for being human administered up to three times a day, preferably as a once or twice a day enteric formulation, (advantageously for being administered up to three times a week, such as two times a week or even as an once a week formulation.).

In the following specification, patient suffering or at risk from suffering troubles from a disease or degenerative disease selected from the group consisting of cancer, sarcoidosis, Kahler's disease, arthritis, skin disease (skin disease can be for example psoriasis, acne, hypertrophic lupus erythematosus, basal cell carcinoma and squamous cell carcinoma), Alzheimer, Parkinson, amyotrophic lateral sclerosis (ALS), Huntington's disease, AIDS, eye degeneration disease (eye disease can be for example any eye degenerative eye disease, eye macular degeneration, cornea degeneration, glaucoma) designates a mammal suffering or at risk from suffering troubles from a disease or degenerative disease selected from the group consisting of cancer, sarcoidosis, Kahler's disease, arthritis, skin disease (skin disease can be for example psoriasis, acne, hypertrophic lupus erythematosus, basal cell carcinoma and squamous cell carcinoma), Alzheimer, Parkinson, amyotrophic lateral sclerosis (ALS), Huntington's disease, AIDS, eye degeneration disease (eye disease can be for example any eye degenerative eye disease, eye macular degeneration, cornea degeneration, glaucoma), said mammal being advantageously selected from the group consisting of humans, dogs and cats, said mammal being most preferably a human.

The composition of the invention is intended for being administered to a patient suffering or at risk from suffering troubles from a disease or degenerative disease selected from the group consisting of cancer, sarcoidosis, Kahler's disease, arthritis, skin disease (skin disease can be for example psoriasis, acne, hypertrophic lupus erythematosus, basal cell carcinoma and squamous cell carcinoma), Alzheimer, Parkinson, amyotrophic lateral sclerosis (ALS), Huntington's disease, AIDS, eye degeneration disease (eye disease can be for example any eye degenerative eye disease, eye macular degeneration, cornea degeneration, glaucoma).

While not being bound to any theory, it is expected that the formulation of the invention treats or relieves such troubles (i.e. one or more of such troubles, especially a combination of such troubles):

by stimulating the p53 gene function for patients suffering from a degenerative disease, or for patients at risk from suffering from a degenerative disease, or for patients under therapeutic treatment of a degenerative disease, and/or by modulating the basic Fibroblast Growth Factor activity and/or the p53 gene function for patients suffering from a degenerative disease, or for patients at risk from suffering from a degenerative disease, or for patients under therapeutic treatment of a degenerative disease, and/or by modulating the angiogenesis effect for patients suffering from a degenerative disease, or for patients at risk from suffering from a degenerative disease, or for patients under therapeutic treatment of a degenerative disease, and/or by controlling the intestinal human microflora, advantageously by inhibition of the development on the intestinal mucosa of bacteria of the group consisting of *Salmonella, Listeria, Escherichia Coli,* and *Staphylococcus*, and/or advantageously by stimulating lactic acid bacteria development on the intestine mucosa; and/or by a combination of such activities.

Patients at risk from suffering from degenerative disease are among other patients under therapeutic treatment of a degenerative disease, patients who have been treated for a degenerative disease, and patients with a diagnostic of a degenerative disease (for example, before the start of a therapeutic treatment, like a chirurgical intervention, a chemotherapy, etc.).

The formulation of the invention comprises an effective modulating dose of said one or more jojoba components of less than 1000 mg, advantageously less than 500 mg, preferably less than 300 mg, most preferably less than 100 mg and a sufficient amount of at least one pharmaceutically acceptable excipient for ensuring the release or delivery of at least 75% by weight of the said at least one or more jojoba components in the intestine, preferably in the small intestine tract.

In the present specification, "release of one or more jojoba components in or after the small intestine tract" means that the one or more jojoba components is not released within the stomach, but only in the small intestine tract and/or after the small intestine tract, for example in the small or upper intestine tract and/or the lower or large intestine/colon tract. While not being bound to any theory, it is expected that the simmondsins or simmondsin components are spliced off in the intestine (due to the presence of bacteria and/or enzymes), especially in the small intestine by one or more enzymes, especially glycosidases, more specifically β-glucosidases, such as EC 3.2.1.21 β-glucosidases or other like enzymes. The obtained simmondsin aglycons are easily converted by mild acid hydrolysis into said simmondsin metabolites, known as 2,5-dihydroxyphenyl acetic acid and 2-hydroxy-5-methoxyphenyl acetic acid.

The formulation of the invention is thus adapted for administering daily doses varying from less than 1 mg per kg body weight up to 10 mg per body weight, or even more if required. The formulation can also be administered twice or three times a week.

The daily doses of active agent(s) per kg body weight are preferably less than 10 mg, most preferably less than 8 mg, in particular less than 5 mg, such as less than 3 mg, less than 2 mg.

Due to the release of the active agents within the intestine, and not in the stomach, the formulation can be administered as an once a week formulation or as a twice a week formulation, the weekly doses per kg body being advantageously less than 20 mg/week, preferably less than 10 mg/week, such as less than 5 mg/week.

For achieving such controlled release, various technologies are available, for example the technology disclosed in WO2000/003696 "Enteric coated pharmaceutical tablet and method of manufacturing" in the name of Squibb Bristol Meyer. The technology disclosed in said document discloses the preparation of a high drug load enteric coated pharmaceutical composition which includes a core in the form of a tablet and which is comprised of a medicament which is sensitive to a low pH environment of less than 3, such as in the stomach medium, and having an enteric coating formed of methacrylic acid copolymer and a plasticizer. The tablets may be of varying size and may be orally ingested individually or a plurality of tablets sufficient to attain a desired dosage may be encapsulated in a dissolvable capsule. The tablets have excellent resistance to disintegration at pH less than 3 but have excellent drug release properties at pH greater than 4.5.

Suitable technologies for achieving enteric and/or colon delivery or release of jojoba components from the small intestine or upper intestine (thus within the small intestine tract and/or within the large intestine tract) are also disclosed in "Enteric coated HPMC capsules designed to achieve intestinal targeting", Ewart T. Cole et al, International Journal of Pharmaceutics 231 (2002) 83-95; and in "Enteric coated hard gelatin capsules", Professor Karl Thoma et al, Capsugel Library, BAS 145 E 2000.

The release/delivery of the one or more jojoba components in the small intestine tract and/or large intestine tract is preferably corresponding to a substantially immediate release in the small intestine tract, such as in the upper small intestine tract. After the release or delivery in the small intestine tract, the one or more jojoba components will be absorbed by the human via the passage of molecules (jojoba components and/or metabolites and/or degradation product of jojoba component in the intestine medium) through walls of the intestine tract.

For example, the enteric coated pharmaceutical composition in the form of solid dosage forms, like tablets, may be prepared by a process which comprises the steps of mixing the one or more jojoba components, a binder/filler, such as microcrystalline cellulose, a disintegrant, such as sodium starch glycolate, and a first portion of a lubricant, such as magnesium stearate, for compaction, in a tumbling type blender, to prepare a dry blend. The blend is then screened and placed back in the blender for a second blending. The resulting blend is slugged or compacted and then sized to form small granules. A second portion of magnesium stearate lubricant for tableting is then calculated and blended in the tumbling type blender with the screened granules. The resulting blend is then formed into tablets (uncoated) having a desired weight and hardness, as well as the desired one or more jojoba components content.

The tablets may then be coated with an enteric film coating suspension comprising Eudragit L-30-D 55 and plasticizer (diethyl phthalate), using a fluid bed coating apparatus with top spray mode, such as an Aeromatic STREA-1 table top unit, and then dried. During preparation of the film coating suspension, a NaOH solution is added to the suspension until a pH of 5.0±0.1 is obtained. Adjustment of the enteric film coating suspension to pH 5 eliminates the need for a subcoat or insulating layer. The advantage here is that an enteric coating at pH 5 permits relatively rapid breakdown in the intestine since only a small amount of alkalinity is required to bring the pH to 5.5. The suspension pH adjustment to 5±0.1 is not critical. The pH could be adjusted up to 5.4 as may be necessary of a specific formulation. Although a top spray mode fluid bed apparatus is preferred, other suitable spray coating means, including one with a bottom spray, or a pan type coater, may also be utilized.

The human oral formulation of the invention comprises advantageously at least one splicing component selected from the group consisting of enzymes suitable to splice off the glucose moiety of the said at least one jojoba component, bacteria suitable for producing at least one enzyme suitable to splice off the glucose moiety of the at least one jojoba component and mixtures thereof. The quantity of splicing component is advantageously adapted so as to ensure in the body of the patient for splicing off at least 50% (preferably at least 75%, most preferably about 100%) of the glucose moiety of the said at least one jojoba component.

The controlled release formulation or composition of the invention has advantageously one or more of the following characteristics:

The one or more jojoba components are selected in the group consisting of simmondsin components of the general formula I

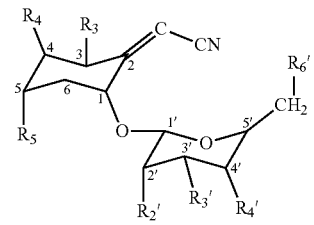

Formula I in which $R_3$, $R_{3'}$, $R_{4'}$, $R_{6'}$ are each OH,
in which $R_2$ is OH or ferulate
in which $R_4$ and $R_5$ are each selected among OH, $OCH_3$ and $OC_2H_5$ or of the general formula II

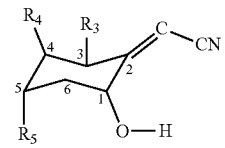

Formula II in which $R_3$ is OH, while $R_4$ and $R_5$ are each selected among OH, $OCH_3$ and $OC_2H_5$, or combinations thereof, the simmondsin components being most preferably a component of formula I.

The components can be in any racemic forms, but is preferably in its levogyre racemic form. The jojoba components can be in the form of a jojoba meal, preferably a defatted jojoba meal.

The formulation of the invention is advantageously adapted for stimulating the p53 gene function, while modulating the angiogenesis effect for patients suffering from a degenerative disease, or for patients at risk from suffering from a degenerative disease, or for patients under therapeutic treatment of a degenerative disease, and preferably for further controlling the intestinal human microflora by inhibition of the development on the intestinal mucosa of bacteria of the group consisting of *Salmonella, Listeria, Escherichia Coli*, and *Staphylococcus*, as well as by stimulating lactic acid bacteria development on the intestine mucosa.

According to an embodiment, the formulation of the invention is adapted for modulating the basic Fibroblast Growth Factor activity, while modulating the angiogenesis effect for patients suffering from a degenerative disease, or for patients at risk from suffering from a degenerative disease, or for patients under therapeutic treatment of a degenerative disease. For example, the basic fibroblast growth factor activity is reduced due to the binding of metabolites and/or by-products of simmondsin compounds formed in the intestine, while inhibiting an angiogenesis effect and/or stimulating the p53 gene function.

It is expected that after being released in the small intestine, the simmondsin component(s) of formula I/II will be subjected to an enzyme action, due to enzyme(s) present within the intestine or on the wall of the intestine, advantageously within the small intestine or wall thereof, for splicing off the glucose moiety. It is thus expected that when splicing off the glucose moiety, the formulation gives a transfer of one glucose for one molecule of simmondsin aglycon or derivate thereof (molecule transfer expected to be carried substantially at the local place of the intestine wall adjacent to the place of the breakdown).

According to an embodiment, in order to ensure a sufficient splicing off, the formulation further comprises an enzyme suitable to splice off the glucose moiety of the simmondsin component(s), said enzyme being advantageously a β-glucosidase, especially a β-glucosidase EC 3.2.1.21, and/or glucose in order to have a molecular ratio glucose/simmondsin component of Formula I comprised between 0.1 and 4, advantageously between 0.5 and 2 or in order to have a molecular ratio glucose/component of formula II comprised between 1.1 and 5, advantageously between 1.5 and 3. When the formulation comprises a plurality of simmondsin components of Formula I and/or II, the glucose molecules will be attributed only once to one component for determining the ratio. When the formulation comprises a mix of component(s) of Formula I and component(s) of Formula II, proportional rule of three can be used for determining the ratio of the mix.

The glucose molecule content should then preferably be comprised between:

0.1×number of molecule of component(s) of formula I+1.1×number of molecule of component(s) of formula II and 4×number of molecule of component(s) of formula I+5×number of molecule of component(s) of formula II The one or more jojoba components are preferably selected in the group consisting of simmondsin components selected from 4,5 didesmethyl simmondsin and 2'-ferulate thereof;
(formula I with $R_3$, $R_{3'}$, $R_{4'}$, $R_{6'}$=OH, $R_{2'}$=OH or ferulate, and $R_4$ and $R_5$=OH)

4-desmethyl simmondsin and 2'-ferulate thereof,
(formula I with $R_3$, $R_{3'}$, $R_{4'}$, $R_{6'}$=OH, $R_{2'}$=OH or ferulate, $R_4$=OH and $R_5$=OCH$_3$)

5-desmethyl simmondsin and 2'-ferulate thereof;
(formula I with $R_3$, $R_{3'}$, $R_{4'}$, $R_{6'}$=OH, $R_{2'}$=OH or ferulate, $R_5$=OH and $R_4$=OCH$_3$)

4,5-dimethyl simmondsin and 2'ferulate thereof,
(formula I with $R_3$, $R_{3'}$, $R_{4'}$, $R_{6'}$=OH, $R_{2'}$=OH or ferulate, $R_4$ and $R_5$=OCH$_3$)

and

Combinations thereof

The formulation further comprises at least one enzyme suitable to splice off the glucose moiety of the simmondsin component(s) or jojoba component(s) and/or one or more bacteria suitable for producing one or more enzymes suitable to splice off the glucose moiety of the simmondsin component(s) or jojoba component(s). The enzyme content will advantageously be present in the formulation at a rate comprised between 5 and 500 units for 50 mg jojoba components, advantageously comprised between 20 and 200 units for 50 mg jojoba components, such as 40, 50, 60, 75, 100, 150 units per 50 mg jojoba components.

The formulation comprises at least one enzyme which is a β-glucosidase enzyme, especially a β-glucosidase EC 3.2.1.21 enzyme and/or at least a bacteria, which is a *lactobacillus* bacteria or a *bifidus* bacteria, especially a lactic acid bacteria, most especially from the *Lactobacillus* family, specifically from the *lactis, plantarum* or *casei* species.

The formulation further comprises a carbohydrate sugar compound having at least one glucose moiety, especially a glucose, advantageously in order to have a molecular ratio glucose or glucose moiety from the carbohydrate sugar/simmondsin component of Formula I comprised between 0.1 and 4, advantageously between 0.5 and 2 and/or in order to have a molecular ratio glucose or glucose moiety from sugar/component of formula II comprised between 1.1 and 5, advantageously between 1.5 and 3.

the formulation of the invention further comprises as at least one carbohydrate sugar compound having at least one glucose moiety, whereby the said at least one carbohydrate sugar compound is present in an amount such that the molecular ratio glucose moiety from the at least one carbohydrate sugar/glucose moiety from the at least one jojoba compound is comprised between 0.05 and 8.

The formulation is an enteric solid or semi solid oral formulation.

The formulation further comprises at least one acetic active agent selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof. The presence of said metabolite or acetic active agent seems to boost the activity of the composition, and even to boost the efficiency of the released at least one jojoba component(s) in the intestine tract, preferably in the small intestine tract. The pharmaceutically acceptable salt is for example a chloride salt.

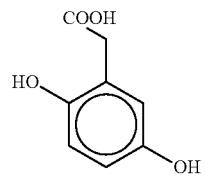 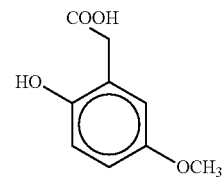

2,5-dihydroxyphenyl acetic acid    2-hydroxy-5-methoxyphenyl acetic acid

While not being bound to any theory, said acetic active agent is expected to boost the splicing off of the glucose moiety of the jojoba component(s) in the intestine/small intestine.

The formulation comprises a dose of less than 100 mg, advantageously less than 50 mg, preferably less than 20 mg, most preferably less than 10 mg of said further acetic active agent, and at least one pharmaceutically acceptable excipient for ensuring the release of at least 75% by weight of the said at least further acetic active agent in the intestine tract, preferably in the small intestine tract.

The weight ratio one or more jojoba components present in the formulation/said further acetic active agent(s) is advantageously greater than 2, preferably greater than 5, most preferably greater than 10, for example comprised between 10 and 100.

- The formulation comprises a sufficient amount of at least one pharmaceutically acceptable excipient for ensuring the release of at least 85% by weight, preferably at least 95% by weight of the said at least one or more jojoba components in the intestine tract, preferably in the small intestine tract, preferably in the upper small intestine tract.
- The formulation comprises a further active agent selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, and a sufficient amount of at least one pharmaceutically acceptable excipient for ensuring the release of at least 85% by weight, preferably at least 95% by weight of the said at least further active agent in the intestine tract, preferably in the small intestine tract.
- The formulation comprises further an acetic active agent selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, and a sufficient amount of at least one pharmaceutically acceptable excipient for ensuring the release or delivery of at least 85% by weight, preferably at least 95% by weight of the said at least one or more jojoba components in the intestine tract, preferably in the small intestine tract, as well as for ensuring the release of at least 85% by weight, preferably at least 95% by weight of the said at least further active agent in the intestine tract, preferably in the small intestine tract. The release of said further active agent is preferably a substantially immediate release in the upper small intestine tract.
- The formulation comprises further an acetic active agent selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof, and a sufficient amount of at least one pharmaceutically acceptable excipient for ensuring the release of at least 75% by weight, preferably at least 85% by weight, most preferably at least 95% by weight of the said at least one or more jojoba components in the intestine tract, preferably in the small intestine tract, as well as for ensuring the release of at least 75% by weight, preferably at least 85% by weight, most preferably at least 95% by weight of the said at least further active agent in the intestine tract, preferably in the small intestine tract, whereby the said at least one acceptable excipient is adapted for ensuring the release of at least 50% of the further active agent in the intestine tract, preferably in the small intestine tract before the start of the release of the said at least one or more jojoba components in the intestine tract, preferably in the small intestine tract. The formulation has a substantially release of the further active agent in the small intestine tract, and a delayed release of the jojoba components in the small intestine tract. Different release moments can be achieved by controlling the thickness of the enteric coating.
- The formulation comprises a further active agent selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof, and a sufficient amount of at least one pharmaceutically acceptable excipient for ensuring the release of at least 75% by weight, preferably at least 85% by weight, most preferably at least 95% by weight of the said at least one or more jojoba components in the intestine tract, preferably in the small intestine tract, as well as for ensuring the release of at least 75% by weight, preferably at least 85% by weight, most preferably at least 95% by weight of the said at least further active agent in the intestine tract, preferably in the small intestine tract, whereby the said at least one acceptable excipient is adapted for ensuring the release of substantially all the further active agent in the intestine tract, preferably in the small intestine tract before the start of the release of the said at least one or more jojoba components in the intestine tract, preferably in the small intestine tract.
- The formulation is adapted for modulating the angiogenesis effect for patient suffering from a degenerative disease, whereby the ratio pro angiogenesis effect/anti angiogenesis effect is comprised between 1:3 and 3:1, advantageously between 1:2 and 2:1.
- The formulation is suitable for treating or relieving troubles from patients suffering from a disease selected from the group consisting of cancer, sarcoidosis, Kahler disease, arthritis, psoriasis, Alzheimer, Parkinson, amyotrophic lateral sclerosis (ALS), Huntington's disease, eye degeneration disease, eye macular degeneration, cornea degeneration, glaucoma and aids, as well as related cancers such as Kaposi sarcoma.
- The formulation is suitable for treating or relieving troubles from patients suffering from a skin disease, advantageously selected from the group consisting of acne, hypertrophic lupus erythematosus, basal cell carcinoma and squamous cell carcinoma.
- The formulation comprises an effective dose of less than 50 mg of one single jojoba component selected in the group consisting of simmondsin components of the general formulae I and II, and is free of other active agents.
- The formulation comprises a semi-solid preparation comprising said at least one or more jojoba components, whereby said semi-solid preparation contains at least two lipidic excipients, at least one of them being hydrophilic having a Hydrophilic Lipidic Balance (HLB) value equal to or greater than 10, the other being an oily vehicle, whereby at least one hydrophilic lipidic excipient(s) with a HLB value of at least 10 is selected from the group consisting of glycerol macrogolglycerides. It has been observed that semi solid preparation enables a quicker bioavailability of the active agent (jojoba components or further active agents), whereby enabling to achieve better treatment results, with low doses.
- The formulation comprises a semi-solid preparation comprising a further active agent selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof, whereby said semi-solid preparation contains at least two lipidic excipients, at least one of them being hydrophilic having a Hydrophilic Lipidic Balance (HLB) value equal to or greater than 10, the other being an oily vehicle, whereby the at least one hydrophilic lipidic excipient(s) with a HLB value of at least 10 is selected from the group consisting of glycerol macrogolglycerides.

The formulation of the invention, wherein at least one hydrophilic lipidic excipient of the composition has an HLB value of at least 12.

The formulation of the invention, wherein at least one hydrophilic lipidic excipient of the composition has an HLB value of at least 13.

The formulation comprises a semi-solid preparation in which the said at least one or more jojoba components and/or further active agent(s) is partially in suspension and/or partially in solution.

The formulation comprises a semi-solid preparation in which the said at least one or more jojoba components and/or further active agent(s) is partially in suspension and partially in solution.

The formulation, wherein the oily vehicle of the preparation is selected from the group consisting of glycerol macrogolglycerides.

The formulation, wherein the oily vehicle of the preparation is selected from the group consisting of vegetable oils, medium chain triglycerides, fatty acid esters, amphiphilic oil, glycerol oleate, and mixtures thereof The formulation, wherein the preparation comprises from 5 to 70% by weight of the oily vehicle selected from the group consisting of vegetable oils, medium chain triglycerides, fatty acid esters, amphiphilic oil, glycerol oleate, and mixtures thereof The formulation, wherein the preparation contains at least one surfactant.

The formulation, wherein the preparation comprises at least one surfactant selected from the group consisting of sorbitan fatty acid esters, polysorbate compounds, polyoxyethylene sorbitan fatty acid esters, sodium laurylsulfate, compounds of lecithin, propylene glycol esters, fatty acid esters of propylene glycol, fatty acid esters of glycerol, polyethylene glycol, and mixtures thereof The formulation, wherein the preparation further comprises from 1 to 10% by weight of at least one additional surfactant.

The formulation, wherein the preparation further comprises at least one disintegrant.

The formulation, wherein at least one disintegrant is selected from the group consisting of povidone, crosspovidone, sodium croscarmellose, and mixtures thereof The formulation, wherein the semi-solid preparation is a semi-solid suspension.

The formulation, wherein the semi-solid suspension is contained in a pharmaceutically-acceptable capsule.

The formulation, in which the capsule is selected from the group consisting of hard gelatin capsules, soft gelatin capsules, hypromellose capsules, and starch capsules, especially enteric coated.

The formulation is in the form of a food supplement or a dietary supplement.

The formulation can be in the form of a enteric coated inner capsule in a enteric coated outer capsule, for example the probiotic being within the inner capsule, while the jojoba component being in the outer capsule and not in the inner capsule.

The formulation is in the form of beads, enteric coated beads. The beads have advantageously a size of less than 2 mm, preferably less than 1 mm, most preferably from 50 µm to 500 µm. The beads, advantageously enteric coated beads can be added/mixed to a probiotic composition, possibly in the form of a liquid or viscous probiotic composition. The beads can be manufactured by using planetizer. The probiotic can also be in the form of beads or solid microspheres. For example the probiotic beads can be prepared by using methods disclosed in EP2648528.

The invention relates also to a human probiotic oral formulation, advantageously for a once or twice a day formulation or as an once a week formulation, twice a week formulation or a three times a week formulation, for stimulating the p53 gene function for patients suffering from a degenerative disease, or for patients at risk from suffering from a degenerative disease, or for patients under therapeutic treatment of a degenerative disease, and/or for modulating the basic Fibroblast Growth Factor activity and/or the p53 gene function for patients suffering from a degenerative disease, or for patients at risk from suffering from a degenerative disease, or for patients under therapeutic treatment of a degenerative disease, and/or for modulating the angiogenesis effect for patients suffering from a degenerative disease, or for patients at risk from suffering from a degenerative disease, or for patients under therapeutic treatment of a degenerative disease, and/or for controlling the intestinal human microflora, advantageously by inhibition of the development on the intestinal mucosa of bacteria of the group consisting of *Salmonella, Listeria, Escherichia Coli,* and *Staphylococcus*, and/or advantageously by stimulating lactic acid bacteria development on the intestine mucosa;

said formulation comprising a dose of one or more jojoba components of less than 1000 mg, advantageously less than 500 mg, preferably less than 300 mg, most preferably less than 100 mg, said one or more jojoba components being advantageously in the form of an enteric formulation according to the invention as disclosed here above, preferably in the form of enteric coated beads, most preferably with a weight average particle size of less than 2 mm.

The jojoba components of formula I/II can be prepared as disclosed in examples 1, 2 and 3.1 of U.S. Pat. No. 7,387,999 (Assignee: D'OOSTERLINCK).

The different components can be isolated the one with respect to the other through HPLC separation.

The following examples of compositions of the invention are given only for example of preferred embodiments.

It has been found that a semi-solid dosage form containing jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, was advantageous for obtaining a good, quick or immediate bioavailability of the jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, in the small intestine tract, preferably in the upper small intestine tract. A semi-solid dosage form containing jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof is a form in which jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof is mixed with suitable melted excipients. The molten mix is then filled for example into hard gelatine capsules or other pharmaceutically acceptable capsules. At ambient temperature (temperature for example of less than 20° C.), the content of the capsule is solid while at temperature higher than 20° C. (for example at temperature greater or equal to 30° C., advantageously greater or equal to 35° C., preferably substantially at body temperature +/−37° C.), it is liquid or semi-solid (paste). The jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof may be solubilized in the mix of excipients or partially solubilized. The active ingredient may also be formulated as a suspension, emulsion or micro emulsion, but preferably like a suspension or micro suspension. Various lipidic excipients are available to the formulator to obtain a semi-solid formulation. Excipients compatible with hard gelatin capsule shells are: lipophilic liquid vehicles (refined specialty oils, medium-chain triglycerides and related esters), semi-solid lipophilic vehicles, solubilizing agents, emulsifying agents and absorption enhancers. The classification of fatty excipients is based on the hydrophilicity or lipophilicity of the excipients, characterized by the hydrophilic/lipophilic balance value (HLB). Examples of lipophilic excipients are vegetable oils (peanut oil, olive oil, soybean oil, and the like), fatty acids (stearic acid, palmitic acid, and the like), fatty alcohols, and the like. Examples of hydrophilic excipients are polyethyleneglycol (PEG) with a molecular weight superior to 3,000. Examples of amphiphilic (=presenting lipophilic and hydrophilic properties) excipients are Poloxamers, Lecithin, PEG esters (GELUCIRE®), and the like.

The advantages of the semi-solid formulations are multiple for jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof: protection of the active ingredient from air and humidity, possibility of increasing the dissolution rate of the molecule and hence of the bioavailability, diminution of the risk of contamination of the operator, diminution of the risk of cross contamination, no possibility of demixing under the effect of vibrational mixing during manufacturing process, facility of the production process. The choice of the nature of the formulation of course influenced the stability of the pharmaceutical form and the bioavailability of the jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof contained in it. Generally, a maximum bioavailability is achieved by preparing and keeping the drug in the amorphous/solubilized state in a solid dispersion or in a lipid-based formulation. For these systems, the barrier we are avoiding is the compound "washing-out" of solution to a large extent into an insoluble crystalline form during the dissolution/release step in vivo.

These systems may consist of suspension, emulsion, micro emulsion, self-emulsifying drug delivery systems or self-emulsifying micro emulsion drug delivery system.

Micro emulsions have the advantage over suspensions such as emulsions and dispersions since thermodynamically they are more stable, that they can be manufactured with little energy input and have generally a longer shelf-life. Nevertheless, a micro emulsion formulation is not a guarantee of higher bioavailability in comparison to suspension as described hereafter.

The formation of oil-in-water (O/W) and water-in-oil (W/O) micro emulsions usually involves a combination of 3-5 basic compounds i.e. oil, surfactant, cosurfactant, water and electrolytes. The challenge is to select for a particular application oil(s) and surfactant(s) that are acceptable from a toxicological perspective and that allow to obtain a high bioavailability of the jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof.

The assessment of the quality of semi-solid lipid based formulations is quite difficult since the in vitro dissolution test is of little help. Indeed, the in vitro/in vivo correlation between dissolution and bioavailability is very poor for this kind of formulations.

The pharmaceutical composition of the invention is an oral semi-solid pharmaceutical composition of jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, containing two lipidic excipients, one of them having an intermediate hydrophilic-lipophilic balance i.e. having a HLB value of at least 10, for example equal to 10, but preferably greater than 10, such as greater or equal to 12, for example comprised between 12 and 14, and the other being an oily vehicle.

The pharmaceutical composition of the invention contains advantageously at least one hydrophilic excipient with a HLB value of at least 10 selected from the group consisting of glycerol macrogolglycerides, polyethyleneglycol derivatives, and mixtures thereof. Preferably, the pharmaceutical composition contains from 20 to 80% by weight of hydrophilic excipient with a HLB value of at least 10 selected from the group consisting of glycerol macrogolglycerides, polyethyleneglycol derivatives, and mixtures thereof.

The oily vehicle is selected from the group consisting of vegetable oils, medium chain triglycerides, fatty acid esters, amphiphilic oil, glycerol oleate derivative, and mixtures thereof. For example, the composition contains from 5 to 70% by weight of an oily vehicle selected from the group consisting of vegetable oils, medium chain triglycerides, fatty acid esters, amphiphilic oil, glycerol oleate derivative, and mixtures thereof.

According to another detail of preferred pharmaceutical compositions of the invention, the composition further contains at least one surfactant, preferably selected from the group consisting of sorbitan fatty acid esters, polysorbate derivatives, polyoxyethylene sorbitan fatty acid esters, sodium laurylsulphate, derivatives of lecithine, propylene glycol esters, fatty acid esters of propylene glycol, fatty acid esters of glycerol, polyethylene glycol, and mixtures thereof. For example, the composition contains from 1 to 10% by weight of at least one surfactant.

Furthermore, the pharmaceutical formulation of the invention contains advantageously at least one disintegrant, preferably selected from the group consisting of povidone derivative, sodium croscarmellose and mixtures thereof.

The pharmaceutical composition of the invention may contain one or more surfactants and/or one or more disintegrants, but contains preferably one or more compounds acting as surfactants and one or more compounds acting as disintegrants.

The invention relates also to a pharmaceutical acceptable capsule containing at least one semi-solid composition of the invention, for example at least one composition of the invention as disclosed here above. The capsule is for example selected from the group consisting of hard gelatine capsules, soft gelatine capsules, hypromellose capsules, starch capsules.

The preferred embodiment of the invention relates thus to a semi-solid formulation of jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof, containing at least 2 lipidic excipients, one of them being an hydrophilic excipient (having a high HLB value namely >10) and the other an oily excipient. The molten mix of these two excipients allows to totally or partially (depending on the ratio between excipients) dissolve jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof. Different kinds of formulations or suspensions of jojoba component(s) of formula I and/or II/further active agents selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof have been formulated. For suspensions, it was possible to dissolve a high fraction of jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof in the mix of excipients and even the whole quantity of the active ingredient if the manufacturing conditions (high temperature and long time of mixing) and the formulations were optimized. Excipients particularly suitable for the dissolution of jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof were lauroyl Macrogol-32 glycerides (GELUCIRE® 44/14, Gattefossé) and Stearoyl Macrogol-32 glycerides (GELUCIRE® 50/13, Gattefossé). When those hydrophilic components are melted together with an oily vehicle, it allows to obtain very stable suspensions—emulsion of jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof in which an important part of the jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof is dissolved. A surfactant may also be added to the formulation to still improve the physical stability of the suspension/emulsion.

Suspension formulations of jojoba component(s) of formula I and/or II/further active agents selected from the group consisting of 2,5-dihydroxyphenyl acetic acid and pharmaceutically acceptable salts thereof, 2-hydroxy-5-methoxyphenyl acetic acid and pharmaceutically acceptable salts and esters thereof, and mixtures thereof are also stable and may give an improved bioavailability of the jojoba component(s) of formula I and/or II/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof.

The effect of different lipophilic excipients was evaluated in the form of semi-solid capsules. The semi-solid capsules were made by addition of the active substance at the pre-melted lipophilic compounds followed by the filling of the liquid into hard gelatin capsule.

The invention relates also to a method for treating a patient suffering or at risk from suffering from a disease selected from the group consisting of cancer, sarcoidosis, Kahler disease, arthritis, skin disease, Alzheimer, Parkinson, amyotrophic lateral sclerosis (ALS), AIDS, Huntington's disease, eye disease, and combinations thereof, said method comprising the step of administering to the patient suffering or at risk from suffering troubles from a disease or degenerative disease, such as disease selected from the group consisting of cancer, sarcoidosis, Kahler disease, arthritis, skin disease (like psoriasis), Alzheimer, Parkinson, amyotrophic lateral sclerosis (ALS), AIDS, Huntington's disease, eye disease or eye degeneration disease, an oral at least partly enteric formulation of the invention, as disclosed in the present specification. Said formulation is for example human administered up to three times a day or up to three times a week, preferably as a once or twice a day enteric formulation or as a once or twice a week formulation, Said formulation comprises advantageously at least: (a) an effective modulating dose of said at least one or more jojoba component of less than 1000 mg, advantageously less than 500 mg, preferably less than 300 mg, most preferably less than 100 mg and a sufficient amount of (b) at least one pharmaceutically acceptable excipient for ensuring the release or delivery of at least 75% by weight of the said at least one or more jojoba component in the intestine, preferably in the small intestine tract, and (c) at least one splicing component selected from the group consisting of enzymes suitable to splice off the glucose moiety of the said at least one jojoba component(s), bacteria suitable for producing at least one enzyme suitable to splice off the glucose moiety of the at least one jojoba component and mixtures thereof.

Advantageously, for a patient having at least one patient's activity selected from the group consisting of p53 gene function, basic Fibroblast Growth Factor activity, angiogenesis activity, intestinal human microflora, intestinal lactic bacteria, and combinations thereof, in which the patient suffering or at risk from suffering troubles from a disease selected from the group consisting of cancer, sarcoidosis, Kahler disease, arthritis, skin disease, Alzheimer, Parkinson, amyotrophic lateral sclerosis (ALS), Huntington's disease, AIDS, eye disease, is orally administered at least once weekly (advantageously at least twice weekly, for example one daily or twice daily) with the said oral formulation of the invention, for controlling at least one patient's activity selected from the group consisting of:

(a) stimulating the p53 gene function for the patients suffering or at risk from suffering troubles from said disease, (b) modulating the basic Fibroblast Growth Factor activity for the patients suffering or at risk from suffering troubles from said disease, (c) modulating the p53 gene function for the patients suffering or at risk from suffering troubles from said disease, (d) modulating the angiogenesis effect for the patients suffering or at risk from suffering troubles from said disease, (e) controlling the intestinal human microflora for the patients suffering or at risk from suffering troubles from said disease, (f) stimulating intestinal lactic acid bacteria development on the intestine mucosa for the patients suffering or at risk from suffering troubles from said disease, and (g) combinations thereof.

The method of the invention uses advantageously a formulation of the invention having one or more of the advantageous details or characteristics of the advantageous or preferred embodiments of the formulation of the invention.

EXAMPLES

The active substance (jojoba component(s) of formula I) with or without one or more further acetic active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof or possibly a defatted jojoba meal) was incorporated into formulations, listed in table 1, consisting of glycerol macrogolglyceride associated with soybean oil or derivative, medium chain triglyceride.

Powder of β-glucosidase EC 3.2.1.21 enzyme was added to each formulation at a rate of about 75 units or BGU. Technical information about β-glucosidase EC 3.2.1.21 enzyme are available on the web site enzymeeducationinstitute.com/enzymes/beta-glucanase/.

The content of β-glucosidase EC 3.2.1.21 enzyme in the formulation can be adapted in function of the patients (humans, dog, cats for example). Said content can advantageously be comprised between 20 and 200 units for 50 mg of Jojoba components.

In said example said enzyme has been used as preferred embodiment for the splicing component. However, other splicing components can be used in the formulation of the invention. Examples of such other splicing components are disclosed in US2015/021603, as fibre degrading enzyme (paragraphs 180 to 303), the content of which is incorporated by reference. The enzyme or bacteria content can be adjusted as required. For example the enzyme content for splicing off the glucose moiety can be as much as 5000 BGU per g jojoba compounds, with preferred content of less than 2000 BGU per g jojoba compounds.

TABLE I

| | Formulations n° (mg) | | | | |
|---|---|---|---|---|---|
| | 1 | 2 | 3 | 4 | 5 |
| Active agent 1 to 29 | 40 | 40 | 40 | 40 | 40 |
| LABRAFIL ® M1944 CS | | 250 | | | |
| GELUCIRE ® 50/02 | | | 198 | | 186 |
| GELUCIRE ® 44/14 | | | 434 | | |
| GELUCIRE ® 50/13 | | | | 140 | 160 | 160 |
| Soy bean oil | | | | 600 | 650 | |
| MIGLYOL ® 812 (*) | 250 | | | | 640 |

(*): info about said compound are available on the following web site: www.petercremerna.com/products/159339301

The formulation was placed in enteric coated hard gelatin or HPMC capsules.

In general, the use of an oily excipient can improve the absorption of lipophilic drug by increasing the solubility of the drug in the lipidic phase, but the release of the active ingredient from the formulation can be slowed down due to the high affinity of the drug for the oily phase.

The use of dispersed systems (emulsions or suspensions) instead of only lipophilic or hydrophilic vehicles, improves the absorption of the drug as well as increasing a larger contact surface.

Concerning the GELUCIRE®, the process of drug release varies according to the HLB of the excipient. GELUCIRE® with high HLB values was found to be the most favourable for a rapid release of the drug (by diffusion and erosion).

The drug release profiles of the formulations 1 to 5 were evaluated in phosphate buffer pH 7.5 with laurylsulfate and pancreatin. The percent of drug released after 4 hours is higher than 60% by weight, such as from 60 to 85% by weight.

The table II gives a series of active agent tested.

TABLE II

Active agent of the formulation of Table I

| Number | Active agent(s) |
|---|---|
| 1 | 40 mg of 4,5 didesmethyl simmondsin + enzyme |
| 2 | 40 mg of 2'-ferulate of didesmethyl simmondsin + enzyme |
| 3 | 40 mg of 4-desmethyl simmondsin + enzyme |
| 4 | 40 mg of 2' ferulate of 4-desmethyl simmondsin + enzyme |
| 5 | 40 mg of 5-desmethyl simmondsin + enzyme |
| 6 | 40 mg of 2'ferulate of 5-desmethyl simmondsin + enzyme |
| 7 | 40 mg of 4,5-dimethyl simmondsin + enzyme |
| 8 | 40 mg of 2' ferulate of 4,5-dimethyl simmondsin + enzyme |
| 9 | 30 mg of 4,5 didesmethyl simmondsin + 10 mg of 2,5-dihydroxyphenyl acetic acid + enzyme |
| 10 | 30 mg of 2'-ferrulate of didesmethyl simmondsin + 10 mg of 2,5-dihydroxyphenyl acetic acid + enzyme |

TABLE II-continued

Active agent of the formulation of Table I

| Number | Active agent(s) |
|---|---|
| 11 | 30 mg of 4-desmethyl simmondsin + 10 mg of 2,5-dihydroxyphenyl acetic acid + enzyme |
| 12 | 30 mg of 2' ferulate of 4-desmethyl simmondsin + 10 mg of 2,5-dihydroxyphenyl acetic acid + enzyme |
| 13 | 30 mg of 5-desmethyl simmondsin + 10 mg of 2,5-dihydroxyphenyl acetic acid + enzyme |
| 14 | 30 mg of 2'ferrulate of 5-desmethyl simmondsin + 10 mg of 2,5-dihydroxyphenyl acetic acid + enzyme |
| 15 | 30 mg of 4,5-dimethyl simmondsin + 10 mg of 2,5-dihydroxyphenyl acetic acid + enzyme |
| 16 | 30 mg of 2' ferulate of 4,5-dimethyl simmondsin + 10 mg of 2,5-dihydroxyphenyl acetic acid + enzyme |
| 17 | 30 mg of 4,5 didesmethyl simmondsin + 10 mg of 2-hydroxy-5-methoxyphenyl acetic acid + enzyme |
| 18 | 30 mg of 2'-ferulate of didesmethyl simmondsin + 10 mg of 2-hydroxy-5-methoxyphenyl acetic acid + enzyme |
| 19 | 30 mg of 4-desmethyl simmondsin + 10 mg of 2-hydroxy-5-methoxyphenyl acetic acid + enzyme |
| 20 | 30 mg of 2' ferulate of 4-desmethyl simmondsin + 10 mg of 2-hydroxy-5-methoxyphenyl acetic acid + enzyme |
| 21 | 30 mg of 5-desmethyl simmondsin + 10 mg of 2-hydroxy-5-methoxyphenyl acetic acid + enzyme |
| 22 | 30 mg of 2'ferulate of 5-desmethyl simmondsin + 10 mg of 2-hydroxy-5-methoxyphenyl acetic acid |
| 23 | 30 mg of 4,5-dimethyl simmondsin + 10 mg of 2-hydroxy-5-methoxyphenyl acetic acid + enzyme |
| 24 | 30 mg of 2' ferulate of 4,5-dimethyl simmondsin + 10 mg of 2-hydroxy-5-methoxyphenyl acetic acid + enzyme |
| 25 | 20 mg of 4,5 didesmethyl simmondsin + 20 mg 4-desmethyl simmondsin + enzyme |
| 26 | 20 mg of 2'-ferrulate of didesmethyl simmondsin + 20 mg of 2' ferulate of 4-desmethyl simmondsin + enzyme |
| 27 | 20 mg of 5-desmethyl simmondsin + 20 mg of 4,5-dimethyl simmondsin + enzyme |
| 28 | 20 mg of 2'ferrulate of 5-desmethyl simmondsin + 20 mg of 2' ferulate of 4,5-dimethyl simmondsin + enzyme |
| 29 | 5 mg of 4,5 didesmethyl simmondsin + 5 mg 4-desmethyl simmondsin + 5 mg of 2'-ferrulate of didesmethyl simmondsin + 5 mg of 2' ferulate of 4-desmethyl simmondsin + 5 mg of 5-desmethyl simmondsin + 5 mg of 4,5-dimethyl simmondsin + 5 mg of 2'ferrulate of 5-desmethyl simmondsin + 5 mg of 2' ferulate of 4,5-dimethyl simmondsin + enzyme |
| 30 | 50 mg of defatted jojoba meal + enzyme |

Stearoyl macrogolglyceride (GELUCIRE® 50/13) known as a drug solubilizer and emulsifying agent of different drugs was advantageously used in association with soybean oil.

This component has the ability to solubilize/emulsify a great part of jojoba component(s) of formula I/further active agents selected from the group consisting of 2,5-dihydroxyphenyl acetic acid and pharmaceutically acceptable salts and esters thereof, 2-hydroxy-5-methoxyphenyl acetic acid and pharmaceutically acceptable salts and esters thereof, and mixtures thereof in the formulation.

The enteric coated hard gelatin capsules with one of the formulation of Table I was used for preparing a formulation suitable for releasing 2,5-dihydroxyphenyl acetic acid and/or 2-hydroxy-5-methoxyphenyl acetic acid, before the release of the simmondsin compounds and/or of the enzyme.

For this purpose a large enteric coated gelatin capsule was first filled with 10 mg 2,5-dihydroxyphenyl acetic acid and/or 2-hydroxy-5-methoxyphenyl acetic acid, and then with a hard gelatin capsule filled with one of the formulation of Table I. This enables an immediate release in the small intestine of 2,5-dihydroxyphenyl acetic acid and/or 2-hydroxy-5-methoxyphenyl acetic acid, before the release of the active agents of the formulations of Table I, and thus before the enzymatic degradation of said active agent(s) within the intestine, especially in the small intestine.

According to another possible embodiment, a large enteric coated gelatin capsule was first filled with 10 mg 2,5-dihydroxyphenyl acetic acid and/or 2-hydroxy-5-methoxyphenyl acetic acid, as well as with the enzyme, and then with a hard gelatin capsule filled with one of the formulation of Table I (with or without enzyme). This enables an immediate release in the small intestine of 2,5-dihydroxyphenyl acetic acid and/or 2-hydroxy-5-methoxyphenyl acetic acid, as well as of the enzyme, before the release of the active simmondsin agents of the formulations of Table I, and thus before the enzymatic degradation of said active agent(s) within the intestine, especially in the small intestine.

While not being bound to any theory, tests made on volunteers (humans) using active agent 29 in the formulation n° 4 of table I in a gelatin capsule adapted to be degraded within the intestine medium, and not in the stomach medium have shown the followings (Some Volunteers received once a day the formulation for 1 week, while some other volunteers received the formulation twice a day for 1 week. Some volunteers suffer from cancer and were under chemo treatment, while others were suffering from arthritis or psoriasis):

the formulation was suitable for modulating the expression of basic Fibroblast Growth Factor, as well as the p53 gene. P53 is a tumour suppressor protein playing an important role in maintaining genomic integrity. By modulating the Basic Fibroblast Growth Factor and the P53 gene, overexpression of basic Fibroblast Growth factor and suppression of the p53 gene could be prevented, while—down expression of basic Fibroblast Growth Factor leads to higher activity of the p53 function. The said modulation activity achieved by the formulations of the invention is considered as modulating therefore the angiogenesis, wound healing, embryonic development and other endocrine signalling pathways.

The formulation of the invention was suitable for modulating/controlling activity of cells, like modulating cell proliferation, survival, migration and differentiation during the development and adult life, whereby preventing many cell disorders, including cancer development, often due to over activated mechanisms.

For the said volunteers, No specific side effects, like bleeding, gastrointestinal bleeding, intolerance, no pain, no swelling, no abdominal or stomach pain, no decreased frequency of urination or amount of urine, no increased thirst, no or low loss of appetite, no nausea or vomiting, no unusual tiredness or weakness, no blood in urine or stools, no chills, no fever, no confusion, no convulsions (seizures), no hallucinations (seeing, hearing, or feeling things that are not there), no hives, no trembling, no difficulty in breathing or swallowing, no dizziness, no fast heartbeat, no irritability, no itching or skin rash, no muscle cramps, no pale skin, no red or irritated eyes, no general feeling of discomfort or illness, no diarrhea, no headache, no loss of hair.

When administered to volunteers under chemotherapeutic treatment, less side effects due to chemotherapeutic treatment/drugs or lower severity of side effects due to chemotherapeutic treatment/drugs. Regular recover could be seen. For volunteers with arthritis and psoriasis improvement could also be observed.

Suitability to control vitamin K activity for keeping and maintaining normal blood clotting factors, when required.

Blood study on volunteers administered with the formulation of the invention has shown the absence of increase of viscosity and without disturbing the normal coagulation pathway. It even seems that the formulation of the invention is effective for restoring the balance between pro coagulant pathways that is responsible for clot formation and mechanisms inhibiting the same beyond the injury site. Even if for some volunteers, the formulation of the invention was able to lower or control the blood viscosity in the human accepted range, such lowering or control was always achieved without increase of bleeding risk, especially gastrointestinal bleeding risk.

It is expected that the enzymatic breakdown of simmondsin components is operated by a first conversion of the simmondsin component into a simmondsin aglycon, followed by some hydrolysis, mild hydrolysis, for forming phenyl acetic acid derivate(s). It is expected that said transformation occurs in the vicinity or inside the intestine wall. It seems also that metabolizing the simmondsin components in vivo after its release in the small intestine from the formulation (for example after breakdown of the gelatin capsule) provides more safe metabolites having no side effects, while being effective. After its enteric release or delivery, the simmondsin compounds can also be broken down by bacteria present in the intestine, especially in the large intestine. It seems also that the enteric release of simmondsin compounds and their breakdown products or metabolites had some control on the activity of bacteria present in the intestine and on normal intestinal microflora, especially on mucosal intestine interface. It seems that intestinal epithelial apical cells surfaces were protected form pathogen attacks, such as due to Salmonella, Listeria, Escherichia Coli, and Staphylococcus, etc. Such control seems to be positive preserving stem cell viability and of the intestine epithelial monolayer integrity.

The formulations of the invention can be administered more than twice a day, for example for initial treatment or co-treatment with the formulations of the invention, or in case treating patient with a body weight of more than 75 kg.

The formulations of the invention can be administered:

for modulating the basic Fibroblast Growth Factor activity and/or the p53 gene function and/or the production of a protein called p21 able to interact with a cell division-stimulating protein (cdk2), for patients suffering from a degenerative disease, or for patients at risk from suffering from a degenerative disease, or for patients under therapeutic treatment of a degenerative disease, and/or for modulating the angiogenesis effect for patients suffering from a degenerative disease, or for patients at risk from suffering from a degenerative disease, or for patients under therapeutic treatment of a degenerative disease.

The formulations of the invention are thus effective for treating various degenerative disease, like cancer, sarcoidosis, Kahler disease, arthritis, psoriasis, Alzheimer, Parkinson and AIDS, but also skin degenerative disease like acne, hypertrophic lupus erythematosus, basal cell carcinoma and squamous cell carcinoma, eye degenerative disease, such as glaucoma.

The formulation seems also to be effective for treating troubles due to autisms.

It has also been seen that the administration of the formulation of the invention with probiotic containing enteric coated capsule was quite interesting for controlling the intestine wall/mucosa microflora. The formulation can be in the form of two distinct capsules, or in the form of a large outer capsule containing a small inner capsule, the outer capsule containing for example the probiotic, for example in the form of a powder, while the inner capsule contains the jojoba component(s).

The formulation of the invention is preferably administered before taking food, but even when taken with food the formulation was effective.

Without being bound to any theory, it seems that patients suffering from degenerative diseases (like cancer, rheumatism) can be effectively be treated by restoring the normal balance between various cellular growth factors and their receptors by the jojoba component(s) (especially simmondsin compound(s) from jojoba) present in the composition of the invention.

Possible causes of degenerative diseases are believed to be due to a patient's content (blood) of various cellular growth factors and their receptors away from the normal balance status. For human, there are more than 20 growth factors and at least 4 different receptor groups for said growth factors, meaning the existence of very complex in-vivo mechanism controlling and regulating the growth and the rejuvenation/renewing of various cells.

Basic Fibroblast growth factor bFGF or FGF-2 is deemed to have an important role in the development, in the evolution, as well as in the regulation of several biochemical in vivo processes, especially for adults or patients aged more than 18 years. Although the bFGF has a predominant role in cells rejuvenation and renewing, the activity of bFGF can be deregulated whereby specific cells can proliferate more than desired population, for example due higher expression of specific receptors of cells, promoting then an extra stimulation and the development of troubles, such as tumours, cancer tumours, inflamed joints or articulations.

The composition of the invention is thus active for controlling the bFGF role, so as to achieve an adequate balance between the positive effect of bFGF and the less positive effect of bFGF, in function of its binding to specific receptor(s).

It has been observed in patients suffering from degenerative troubles, that the composition of the invention was suitable to treat or prevent troubles linked to ageing, genetic predisposition/variation, reactive and/or resistant to specific compounds, for example to toxic compounds, for example due to deficit in specific essential nutrients, for example due to inappropriate foods and/or due to inappropriate lifestyle habits, and more specifically linked to a plurality of such factors.

It is admitted that overload of muscles (causing production of lactic acid) as well inappropriate feeding have an important role in acid formation in the body, said acid formation causing then a stimulation of the activity of bFGF and VEGF (vascular Endothelial Growth Factor), which can then lead to over stimulation of angiogenesis, and to a suppression of the activity of p53 tumour suppressor. It has been observed from patients suffering from degenerative diseases that the composition of the invention was able to control the stimulation of angiogenesis, and to prevent a suppression of the activity of p53 tumour suppressor.

Angiogenesis is a process through which new blood vessels are formed. In normal conditions, angiogenesis has an important role when a high amount of nutriments is flowing to tissues, such as foetal development, wound healing or zones of the body where a lack of oxygen occurs due to bad or insufficient blood circulation. For specific disease, disorders or conditions, diseased cells can stimulate themselves angiogenesis, mostly stimulated by VEGF which on its side will be stimulated by bFGF. A too abundant production or formation of small blood vessels can lead to swelling or tumours, pain and even articulation damages, as appearing in rheumatism troubles. Tumours will also be associated with new small blood vessels, whereby said tumours will have a higher blood circulation enabling said tumours to have access to a higher amount of nutriments and oxygen, whereby causing a quicker growth of said tumours and a quicker propagation (metastasis) into the body via the blood circulation system.

The composition of the invention is suitable for controlling/reducing the growth of tumours, whereby reducing the propagation risks of diseased cells within the whole body, as well the growth of tumours.

The p53 tumour suppressing protein is active for cell division to control DNA replication. DNA errors can lead to cancer. The p53 is active for repairing damaged DNA and/or for eliminating/destroying cells with damaged DNA. An increase of the p53 activity lead thus to a better body protection and is acting against the formation and propagation of cancerous cells. The composition of the invention is promoting the activity of p53 protein, while suppressing the formation of new blood vessels.

An over stimulation due to bFGF and over stimulation of angiogenesis or production of small blood vessels and a lowering of the p53 activity (meaning lower control of DNA errors) are causes or inter related causes for the development of degenerative diseases, like cancer and rheumatism. It has further to point out that patients suffering from rheumatism have a higher risk to develop cancer troubles, than patients not suffering from rheumatism. The composition of the invention is thus suitable especially for patients suffering from rheumatism, so as to prevent or reduce the risk of the occurrence of cancerous cells or the proliferation and propagation of such cancerous cells, especially in the whole body.

The composition of the invention is suitable for treating patients suffering from troubles caused by occurring from distorted or abnormal cells growth factors balance, as well as for preventing patients from suffering from troubles caused by occurring from distorted or abnormal cells growth factors balance, the said composition of the invention acting as means for repairing or restoring the cell growth factors balance within the human normal value range; as means for suppressing or restraining the over stimulation of bFGF cells, as means for suppressing or restraining the excessive angiogenesis within human normal range value, and as means for increasing or improving or catalysing the activity of p53 within human normal range value. The composition of the invention has a quite quick action (possibly due to some blood thinning effect), meaning that it can be considered that the active agent ("jojoba component(s)") is a catalysis promoting the in vivo p53 activity, while suppressing or restraining over stimulation of bFGF and/or angiogenesis, and preventing proliferation and propagation of diseased cells within the whole body.

The composition of the invention comprises active jojoba component(s), such as specific metabolite(s) of simmondsin or metabolite(s) of jojoba, which is/are active to repair or restore abnormal bFGF balance, for binding to bFGF receptor sites of in vivo cells, especially to cells related to degenerative diseases, such as cancer and rheumatism.

Some tests have also been carried out on dogs and cats suffering from degenerative disease (cancer like). The tested animals showed a reduction/inhibition of the growth of cancerous cells.

It has been observed that the composition of the invention, while being efficient for treating troubles due to degenerative diseases or for preventing such troubles, was acting as suppressing or restraining some side effects appearing when the patient is treated by chemotherapy or with classical rheumatism drugs.

What we claim is:
1. A method of treating a mammal suffering from a disease selected from the group consisting of cancer, sarcoidosis, Kahler disease, arthritis, skin disease, Alzheimer, Parkinson, amyotrophic lateral sclerosis (ALS), Huntington's disease, AIDS, eye disease and combinations thereof, said method comprising administering at least once a week to the mammal, an oral or at least partly enteric formulation comprising at least one jojoba component comprising a glucose moiety selected in the group consisting of:
(a) simmondsin components of the general formula I

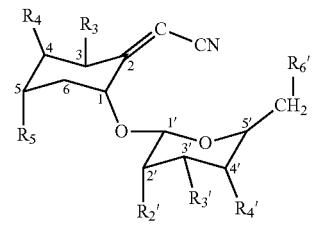

in which $R_3$, $R_{3'}$, $R_{4'}$, $R_{6'}$ are each OH,
in which $R_2$ is OH or ferulate, and
in which $R_4$ and $R_5$ are each selected from the group consisting of OH, $OCH_3$, and $OC_2H_5$;

(b) simmondsin comnonents of the general formula II

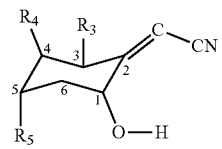

in which $R_3$ is OH, while $R_4$ and $R_5$ are each selected from the group consisting of OH, $OCH_3$ and $OC_2H_5$; and combinations thereof, said formulation comprising at least: (a) an effective modulating dose of the at least one jojoba component of less than 1000 mg, (b) at least one pharmaceutically acceptable excipient for ensuring the release or delivery of at least 75% by weight of the at least one jojoba component in the intestine, and (c) at least one splicing component selected from the group consisting of enzymes suitable to splice off the glucose moiety of the at least one jojoba component, bacteria suitable for producing at least one enzyme suitable to splice off the glucose moiety of the at least one jojoba component and mixtures thereof.

2. The method of claim 1, in which the formulation comprises at least one jojoba component selected in the group consisting of simmondsin components of the general formula I:

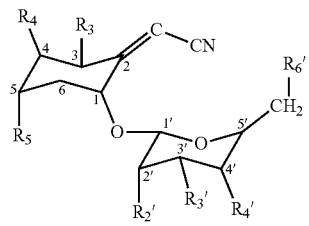

in which $R_3$, $R_{3'}$, $R_{4'}$, $R_{6'}$ are each OH,
in which $R_{2'}$ is OH or ferulate, and
in which $R_4$ and $R_5$ are each selected from the group consisting of OH, $OCH_3$, and $OC_2H_5$.

3. The method of claim 1, in which the formulation comprises at least one jojoba component selected from the group consisting of 4,5 didesmethyl simmondsin and 2'-ferulate thereof; 5-desmethyl simmondsin and 2-ferulate thereof; 4-desmethyl simmondsin and 2'-ferulate thereof; 4,5-dimethyl simmondsin and 2'ferulate thereof; and combinations thereof.

4. The method of claim 1, in which the formulation comprises as the splicing component, a *Lactobacillus* bacteria of the species selected from the group consisting of lactis species, plantarum species and casei species.

5. The method of claim 1, wherein said formulation further comprises as at least one carbohydrate sugar compound having at least one glucose moiety, whereby the said at least one carbohydrate sugar compound is present in an amount such that the molecular ratio glucose moiety from the at least one carbohydrate sugar/glucose moiety from the at least one jojoba compound is comprised between 0.05 and 8.

6. The method of claim 1, wherein said formulation further comprises an acetic active agent selected from the group consisting of 2,5-dihydroxyphenyl acetic acid, pharmaceutically acceptable salts and esters of 2,5-dihydroxyphenyl acetic acid, 2-hydroxy-5-methoxyphenyl acetic acid, pharmaceutically acceptable salts and esters of 2-hydroxy-5-methoxyphenyl acetic acid, and combinations thereof.

7. The method of claim 1, in which the formulation is provided with at least one pharmaceutically acceptable excipient for ensuring the release of at least 85% by weight of the said at least one jojoba component and of the splicing component in the intestine tract.

8. The method of claim 6, in which the formulation is provided with at least one pharmaceutically acceptable excipient present in the formulation in an amount ensuring the release of at least 85% by weight of the said at least one acetic active agent in the intestine tract.

9. The method of claim 8, in which the said at least one pharmaceutically acceptable excipient is adapted for ensuring the release of at least 50% of the further acetic active agent in the intestine tract, before the start of the release of the said at least one jojoba component in the intestine tract.

10. The method of claim 1, wherein said formulation is a semi-solid oral preparation comprising the at least one jojoba component, whereby said semi-solid oral preparation contains at least two lipidic excipients, at least one of them being hydrophilic having a Hydrophilic Lipidic Balance (HLB) value equal to or greater than 10, the other being an oily vehicle, whereby at least one hydrophilic lipidic excipient(s) with a HLB value of at least 10 is selected from the group consisting of glycerol macrogolglycerides.

11. The method of claim 1, in which the formulation comprises as the splicing component, a component selected from the group consisting of β-glucosidase enzyme, lactobacillus bacteria, bifidus bacteria and combinations thereof.

12. The method of claim 1, in which the formulation comprises as the splicing component, a component selected from the group consisting of β-glucosidase EC 3.2.1.21 enzyme, lactic acid bacteria, and combination thereof.

13. The method of claim 1, in which the formulation is orally administered at least once a week to the mammal as a food supplement.

14. The method of claim 1, in which the mammal is selected from the group consisting of humans, dogs and cats.

15. The method of claim 1, in which the formulation is orally administered to the mammal.

* * * * *